United States Patent [19]

Takaya et al.

[11] Patent Number: 4,515,788

[45] Date of Patent: May 7, 1985

[54] CEPHEM COMPOUNDS

[75] Inventors: Takao Takaya, Kawanishi; Hisashi Takasugi, Hamaguchinishi; Hideaki Yamanaka, Hirakata, all of Japan

[73] Assignee: Fujisawa Pharmaceutical Co., Ltd., Osaka, Japan

[21] Appl. No.: 402,256

[22] Filed: Jul. 27, 1982

[30] Foreign Application Priority Data

Aug. 3, 1981 [GB] United Kingdom ............... 8123683
Oct. 16, 1981 [GB] United Kingdom ............... 8131261

[51] Int. Cl.$^3$ .................................... C07D 501/20
[52] U.S. Cl. .................................... 514/202; 544/22; 544/23; 544/28; 544/27; 548/204
[58] Field of Search .......... 424/246; 544/22, 27, 544/28, 23

[56] References Cited

U.S. PATENT DOCUMENTS

| | | | |
|---|---|---|---|
| 3,971,778 | 7/1976 | Cook et al. | 544/30 |
| 4,263,291 | 4/1981 | Takaya et al. | 424/246 |
| 4,282,220 | 8/1981 | Bormann et al. | 544/28 |
| 4,287,193 | 9/1981 | Heymes et al. | 544/27 |

FOREIGN PATENT DOCUMENTS 55-133385 10/1980 Japan .

Primary Examiner—Paul M. Coughlan, Jr.
Attorney, Agent, or Firm—Oblon, Fisher, Spivak, McClelland & Maier

[57] ABSTRACT

This invention relates to novel compounds of high antimicrobial activity of the formula:

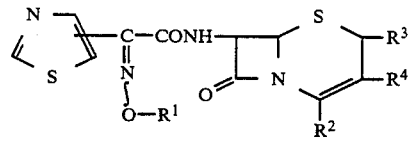

wherein
$R^1$ is carboxy(lower)alkyl or protected carboxy(lower)alkyl,
$R^2$ is carboxy or protected carboxy,
$R^3$ is hydrogen or lower alkyl, and
$R^4$ is lower alkyl, lower alkoxy, acyloxymethyl, lower alkylthiomethyl, lower alkoxymethyl, halogen, lower alkenyl or hydrogen,
and pharmaceutically acceptable salts thereof.

6 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms, especially for oral administration.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula:

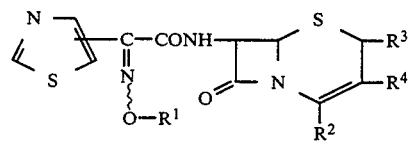

(I)

wherein
$R^1$ is carboxy(lower)alkyl or protected carboxy(lower)alkyl,
$R^2$ is carboxy or protected carboxy,
$R^3$ is hydrogen or lower alkyl, and
$R^4$ is lower alkyl, lower alkoxy, acyloxymethyl, lower alkylthiomethyl, lower alkoxymethyl, halogen, lower alkenyl or hydrogen.

According to the present invention, the new cephem compounds (I) can be prepared by various processes which are illustrated in the following scheme.

Process 1

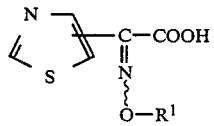

(III)
or its reactive derivative
at the carboxy group
or a salt thereof

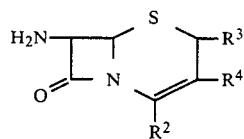

(II)
or its reactive derivative
at the amino group
or a salt thereof
⟶

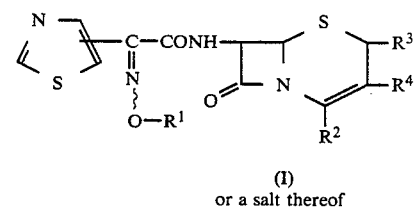

(I)
or a salt thereof

Process 2

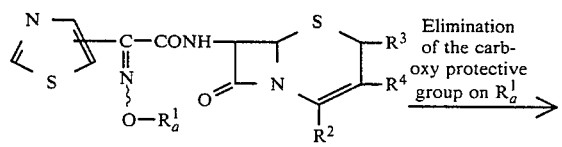

Elimination of the carboxy protective group on $R_a^1$ ⟶

(Ia)
or a salt thereof

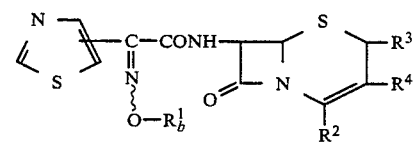

(Ib)
or a salt thereof

Process 3

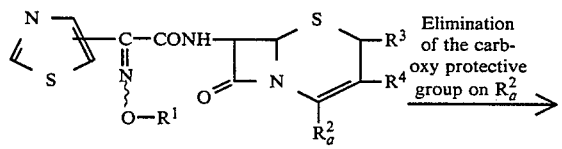

Elimination of the carboxy protective group on $R_a^2$ ⟶

(Ic)
or a salt thereof

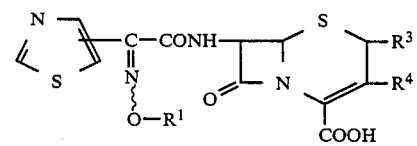

(Id)
or a salt thereof

Process 4

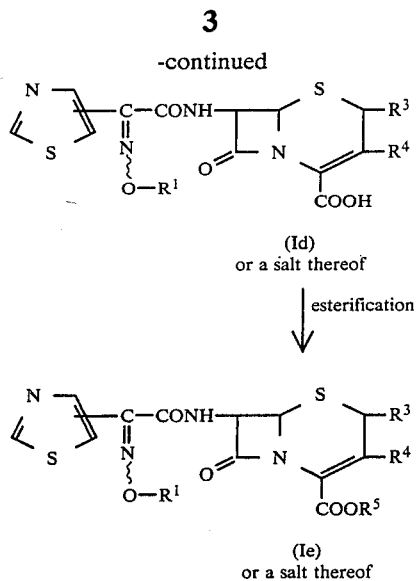

(Id)
or a salt thereof

↓ esterification (Ie)
or a salt thereof wherein
R¹, R², R³ and R⁴ are each as defined above,
$R_a^1$ is protected carboxy(lower)alkyl,
$R_b^1$ is carboxy(lower)alkyl,
$R_a^2$ is protected carboxy, and
R⁵ is ester moiety of esterified carboxy represented by a group of the formula:

The starting compound (III) is novel and can be prepared by the processes as illustrated by the following scheme.

Process A

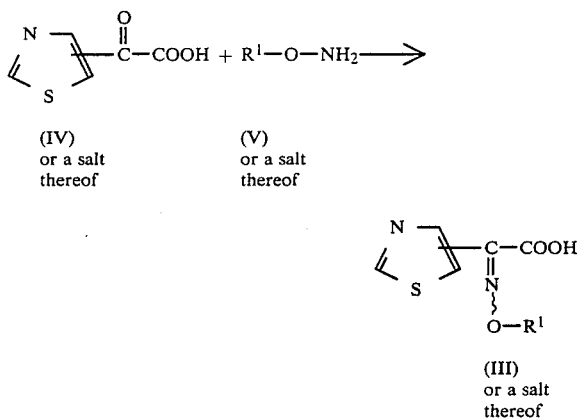

Process B

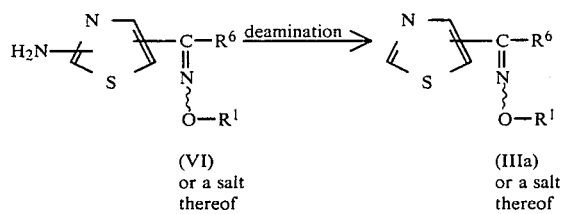

Process C

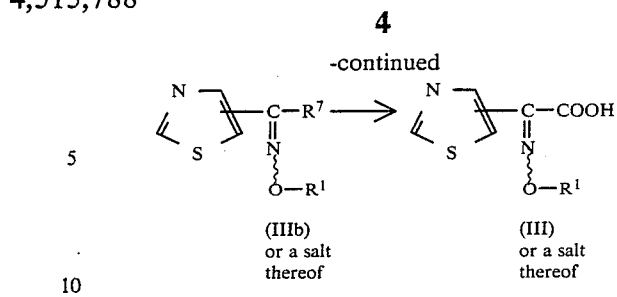

(IIIb)
or a salt thereof (III)
or a salt thereof wherein
R¹ is as defined above,
R⁶ is carboxy or protected carboxy, and
R⁷ is protected carboxy.

In the present invention with regard to the object compounds (I) and (Ia)~(Ie) and the other compounds (III), (IIIa), (IIIb) and (VI), it is to be understood that all of said compounds include syn isomer, anti isomer and a mixture thereof. And, as to the object compound (I), the syn isomer thereof means one geometrical isomer having the group represented by the following formula:

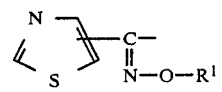

(wherein R¹ is as defined above)
and the anti isomer means the other geometrical isomer having the group of the formula:

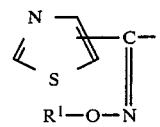

(wherein R¹ is as defined above).

Further, as to the other compounds, the syn and anti isomers thereof also are represented by the same geometrical configuration as that of the object compound (I), respectively.

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected carboxy" and "protected carboxy moiety" in the term "protected carboxy(lower)alkyl" may include an esterified carboxy and the like.

Suitable examples of the ester moiety in said esterified carboxy and ester moiety of esterified carboxy represented by a group of the formula: —COOR⁵ may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. etynyl ester, propynyl ester, etc.); ar(lower)alkyl ester [e.g., mono(or di or tri)-phenyl(lower)alkyl ester, etc.] which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.), and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.), lower alkanoyloxy(lower)alkoxycarbonyl [e.g., acetoxymethoxycarbonyl, pivaloyloxymethoxycarbonyl, hexanoyloxymethoxycarbonyl, 1(or 2)-propionyloxyethoxycarbonyl, etc.], lower alkoxycarbonyloxy(lower)alkoxycarbonyl (e.g. methoxycarbonyloxymethoxycarbonyl, 1-ethoxycarbonyloxyethoxycarbonyl, 1-isopropoxycarbonyloxyethoxycarbonyl, etc.), (5-lower alkyl-2-oxo-1,3-dioxol-4-yl)(lower)alkoxycarbonyl [e.g. (5-methyl-2-oxo-1,3-dioxol-4-yl)methoxycarbonyl, etc.], ar(lower)alkoxycarbonyl [e.g. mono(or di or tri)phenyl(lower)alkoxycarbonyl, etc.] which may have at least one suitable substituent(s) (e.g. benzyloxycarbonyl, 4-methoxybenzyloxycarbonyl, 4-nitrobenzyloxycarbonyl, phenethyloxycarbonyl, trityloxycarbonyl, benzhydryloxycarbonyl, etc.) and the like.

Suitable "lower alkyl" and "lower alkyl moiety" in the terms "carboxy(lower)alkyl", "protected carboxy(lower)alkyl" and "lower alkylthiomethyl" may include methyl, ethyl, propyl, isopropyl, butyl, t-butyl, pentyl, hexyl and the like, preferably one having 1 to 4 carbon atom(s).

Suitable "lower alkoxy" and "lower alkoxy moiety" in the term "lower alkoxymethyl" may include methoxy, ethoxy, propoxy, isopropoxy, butoxy, t-butoxy, pentyloxy, hexyloxy and the like, preferably one having 1 to 4 carbon atom(s).

Suitable "acyl" in the term "acyloxymethyl" may be aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, pivaloyl, etc.), preferably one having 1 to 4 carbon atom(s);

lower alkoxycarbonyl (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.);

lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, naphthoyl, phthaloyl, indancarbonyl, etc.);

ar(lower)alkanoyl (e.g. phenylacetyl, phenylpropionyl, etc.);

ar(lower)alkoxycarbonyl (e.g. benzyloxycarbonyl, phenethyloxycarbonyl, etc.); or the like.

Preferable example of the acyl may be lower alkanoyl (e.g. formyl, acetyl, propionyl, butyryl, isobutyryl, valeryl, isovaleryl, pivaloyl, etc.) or the like.

Suitable "halogen" may be chlorine, bromine, iodine or fluorine.

Suitable "lower alkenyl" may include vinyl, 1-propenyl, allyl, 1 or 2 or 3-butenyl, 1 or 2 or 3 or 4-pentenyl, 1 or 2 or 3 or 4 or 5-hexenyl and the like, preferably one having 2 to 4 carbon atoms.

Preferable embodiments of the object compound (I) are as follows.

Preferred embodiment of $R^1$ is carboxy(lower)alkyl or esterified carboxy(lower)alkyl [more preferably lower alkoxycarbonyl(lower)alkyl or mono(or di or tri)-phenyl(lower)alkoxycarbonyl(lower)alkyl];

$R^2$ is carboxy or esterified carboxy [more preferably mono(or di or tri)phenyl(lower)alkoxycarbonyl which may have a nitro, lower alkanoyloxy(lower)alkoxycarbonyl, lower alkoxycarbonyloxy(lower)alkoxycarbonyl or (5-lower alkyl-2-oxo-1,3-dioxol-4-yl)(lower)alkoxycarbonyl];

$R^3$ is hydrogen or lower alkyl (most preferably methyl); and $R^4$ is lower alkyl (most preferably methyl), lower alkoxy (most preferably methoxy), lower alkanoyloxymethyl (most preferably acetoxymethyl), lower alkylthiomethyl (most preferably methylthiomethyl), lower alkoxymethyl (most preferably methoxymethyl), halogen (most preferably chlorine, lower alkenyl (most preferably vinyl) or hydrogen.

The processes for preparing the object compounds of the present invention are explained in details in the following.

Process 1

The object compound (I) or a salt thereof can be prepared by reacting the compound (II) or its reactive derivative at the amino groups or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, trimethylsilylacetamide or the like; a derivative formed by reaction of the compound (II) with phosphorus trichloride or phosgene, and the like.

Suitable salt of the compound (II) may include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid etc.), and the like.

Suitable salt of the compound (III) can be referred to the ones exemplified for Compound (I).

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, 4-nitrophenyl ester, 2,4-dinitrophenyl ester, trichlorophenyl ester, pentachlorophenyl ester, mesyl phenyl ester, phenylazophenyl ester, phenyl thioester, 4-nitrophenyl thioester, 4-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like.

These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hyroxybenzisoxazolium salt; 2-ethyl-5-(m-sulfophenyl)-isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

Process 2

The object compound (Ib) or a salt thereof can be prepared by subjecting the compound (Ia) or a salt thereof to elimination reaction of the carboxy protective group on $R_a{}^1$.

Suitable salt of the compounds (Ia) and (Ib) can be referred to the ones exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). The acidic hydrolysis using trifluoroacetic acid is usually accelerated by addition of anisole.

The reaction is usually carried out in a solvent such as water, methylene chloride, an alcohol (e.g. methanol, ethanol, etc.), a mixture thereof or any other solvent which does not adversely influence the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like.

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually carried out in a solvent such as water, alcohol (e.g. methanol, ethanol, etc.), N,N-dimethylformamide, tetrahydrofuran, a mixture thereof or any other solvent which does not adversely affect the reaction.

Additionally, in case that the above-mentioned acids to be used in chemical reduction are in liquid, they can also be used as a solvent.

The reaction temperature of this reduction is not critical and the reaction is usually carried out under cooling to warming.

The present invention includes, within its scope, the case that the protected carboxy group in $R^2$ are converted into the free carboxy group during this reaction or the post-treating step of this reaction.

Process 3

The object compound (Id) or a salt thereof can be prepared by subjecting the compound (Ic) or a salt thereof to elimination reaction of the carboxy protective group on $R_a{}^2$.

Suitable salts of the compounds (Ic) and (Id) can be referred to the ones exemplified for the compound (I).

The present elimination reaction can be carried out in a similar manner to that of aforementioned

Process 2

Process 4

The object compound (Ie) or a salt thereof can be prepared by subjecting the compound (Id) or a salt thereof to esterification reaction.

Suitable salt of the compound (Ie) can be referred to the ones exemplified for the compound (I).

The present reaction may be carried out by reacting the compound (Id) or a salt thereof with esterifying agent.

Suitable esterifying agent may be a compound of the formula:

wherein
$R^5$ is as defined above, and
X is hydroxy or its reactive derivative.

Suitable reactive derivative of hydroxy for X may include an acid residue such as aforesaid halogen or the like.

The present reaction is usually carried out in a solvent such as dimethylformamide, pyridine, hexamethylphosphoric triamide, dimethylsulfoxide or any other solvent which does not adversely affect the reaction.

In case that the compound (Id) is used in a form of free acid, the reaction is preferably carried out in the presence of a base as mentioned in Process 2.

The reaction temperature is not critical and the reaction is preferably carried out under cooling, at ambient temperature or under warming.

In case that the object compound (I) has free carboxy group(s), it may be transformed into its pharmaceutically acceptable salts by a conventional method. The process for the preparation of the starting compound is explained in details in the following.

Process A

The compound (III) or a salt thereof can be prepared by reacting the compound (IV) or a salt thereof with the compound (V) or a salt thereof.

Suitable salt of the compound (IV) may include the same ones as exemplified for the compound (I).

Suitable salt of the compound (V) may include the same ones as exemplified for the compound (II).

The reaction is usually carried out in a conventional solvent which does not adversely influence the reaction such as water, alcohol (e.g. methanol, ethanol, propanol, etc.), dioxane, tetrahydrofuran, etc., or a mixture thereof. The reaction temperature is not critical and the reaction is usually carried out under cooling to heating.

Process B

The compound (IIIa) or a salt thereof can be prepared by subjecting the compound (VI) or a salt thereof to deamination reaction.

Suitable salt of the compound (VI) may include the same ones as exemplified for the compound (II).

Suitable salt of the compound (IIIa) may include the same ones as exemplified for the compound (I). The reaction is carried out by reacting the compound (VI) or a salt thereof with an alkali metal nitrite (e.g. sodium nitrite, potassium nitrite, etc.) or lower alkyl nitrite (e.g. t-butyl nitrite, isopentyl nitrite, etc.).

This reaction is usually carried out in a conventional solvent which does not adversely influence the reaction such as tetrahydrofuran, N,N-dimethylformamide, etc..

The reaction temperature is not critical and the reaction is usually carried out under room temperature to heating around boiling point of the solvent.

Process C

The object compound (III) or a salt thereof can be prepared by subjecting the compound (IIIb) or a salt thereof to elimination reaction of the carboxy protective group on $R^7$. This reaction is carried out in a similar manner to that of Process 2 as mentioned above.

The object compound (I) and pharmaceutically acceptable salt thereof of the present invention are novel compounds which exhibit high antibacterial activity and inhibit the growth of a wide variety of pathogenic microorganisms including Gram-positive and Gram-negative bacteria and are useful as anti-microbial agents, especially for oral administration. For therapeutic purpose, the compounds according to the present invention can be used in the form of pharmaceutical preparation which contain said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, ointments or suppositories, solutions, suspension, emulsions, and the like. If desired, there may be included in the above preparations auxiliary substances, stabilizing agents, wetting or emulsifying agents, buffers and other commonly used additives.

While the dosage of the compounds will vary dependent upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the objject compound, anti-microbial activities, urinary excretion and biliary excretion of a representative compound of the present invention are shown below.

[1] Test Compound

7-[2-Carboxymethoxyimino-2-(4-thiazoly)-acetamido]-3-cephem-4-carboxylic acid (syn isomer). (hereinafter referred to as compound A )

[2] Test (A) Minimal inhibitory concentrations

1 Test Method

In vitro antibacterial activity was determined by the two-fold argar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

2 Test Results

| Test strains | MIC (μg/ml) |
| Compound | Compound A |
| --- | --- |
| Klebsiella pneumoniae 7 | 0.05 |
| Proteus mirabilis 18 | 0.05 |

(B) Urinary excretion

1 Test Method

Urine of rats was collected with a urine collector at 0 to 6, and 6 to 24 hours after oral administration of 100 mg/kg of the test antibiotic. The antibiotic levels in the urine samples were bioassayed with the standard solution prepared with M/15 phosphate buffer (pH 7.0) and the urinary recovery in 24 hours was calculated.

2 Test Result

|  | Urinary recovery in 24 hours (%) |
| --- | --- |
| Compound A | 43.5 |

(C) Biliary excretion

1 Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 100 mg/kg of the test antibiotic. The antibiotic levels in the bile samples were bioassayed with the standard solution prepared with M/15 phosphate buffer (pH 7.0) and the biliary recovery in 24 hours were calculated.

2 Test Result

|  | Biliary recovery in 24 hours (%) |
| --- | --- |
| Compound A | 7.9 |

The following Preparations and Examples are given for the purpose of illustrating the present invention.

Preparation 1

A mixture of 2-t-butoxycarbonylmethoxyimino-2-(2-formamidothiazol-4-yl)acetic acid (syn isomer) (15.0 g) and conc. hydrochloric acid (9.5 g) in methanol (75 ml) was stirred at ambient temperature for 2.5 hours. Water (100 ml) was added to the reaction mixture and the solution was adjusted to pH 3.0 with 10% aqueous solution of sodium hydroxide under stirring. The precipitates were collected by filtration, washed with water and diisopropyl ether and dried to give 2-t-butoxycarbonylmethoxyimino-2-(2-aminothiazol-4-yl)acetic acid (syn isomer) (12.7 g).

IR (Nujol): 3340, 1740, 1630 cm$^{-1}$

NMR (DMSO-d$_6$, δ): 1.43 (9H, s), 4.51 (2H, s), 6.77 (3H, s)

Preparation 3

To a suspension of 2-t-butoxycarbonylmethoxyimino-2-(2-aminothiazol-4-yl)acetic acid (syn isomer) (11.5 g) in tetrahydrofuran (80.5 ml) was added dropwise a solution of t-butyl nitrite (6.5 g) in tetrahydrofuran (32.5 ml) at 50° to 57° C. under stirring, and the mixture was stirred at 50° to 55° C. for 20 minutes. The reaction mixture was poured into a mixture of ethyl acetate and water and the solution was acidified to pH 1.0 with 10% hydrochloric acid. Water (60 ml) was added to the separated organic layer and the mixture was adjusted to pH 6.0 with 40% aqueous solution of potassium carbonate. The separated aqueous solution was washed with ethyl acetate and the solution was acidified to pH 2.8 with 10% hydrochloric acid. The acidified solution was extracted with ethyl acetate and the ethyl acetate layer was dried over magnesium sulfate and evaporated. The residue was triturated with diisopropyl ether to give 2-t-butoxycarbonylmethoxyimino-2-(4-thiazolyl)acetic acid (syn isomer) (6.1 g), mp. 141° C. (dec.).

IR (Nujol): 1730 cm$^{-1}$

NMR (DMSO-d$_6$, δ): 1.46 (9H, s), 4.69 (2H, s), 8.08 (1H, d, J=2.0 Hz), 9.21 (1H, d, J=2.0 Hz)

Preparation 3

A solution of isopentyl nitrite (5.9 ml) in tetrahydrofuran (50 ml) was dropwise added to a mixture of 2-(2-aminothiazol-4-yl)-2-(benzhydryloxycarbonyl-methoxyimino)acetic acid (syn isomer) (10.6 g) in tetrahydrofuran (100 ml) at 50° to 55° C. under stirring and the mixture was stirred at 55° to 60° C. for 30 minutes. Tetrahydrofuran was evaporated in vacuo. The residue was dissolved in a mixture of ethyl acetate and water and the mixture was adjusted to pH 7.5 with 20% aqueous solution of potassium carbonate. The separated aqueous layer was adjusted to pH 2.0 with 10% hydrochloric acid and extracted with ethyl acetate. The extract layer was washed with saturated aqueous solution of sodium chloride, dried over magnesium sulfate and evaporated to give 2-(benzhydryloxycarbonylmethoxyimino)-2-(4-thiazolyl)acetic acid (syn isomer) (4.9 g).

IR (Nujol): 1735 cm$^{-1}$

NMR (DMSO-d$_6$, δ): 4.96 (2H, s), 6.90 (1H, s), 7.18–7.58 (10H, m), 8.03 (1H, d, J=2.0 Hz), 9.18 (1H, d, J=2.0 Hz)

Preparation 4

A mixture of 2-(4-thiazolyl)glyoxylic acid (2.3 g) in methanol (23 ml) and t-butyl 2-aminooxyacetate (2.6 g) was stirred for an hour at ambient temperature. The reaction mixture was added to a mixture of ethyl acetate and water and adjusted to pH 7.5 with saturated aqueous solution of sodium bicarbonate. The separated aqueous layer was adjusted to pH 2.0 with 10% hydrochloric acid and the mixture was saturated sodium chloride. The acidic mixture was extracted with ethyl acetate. The extract layer was washed with saturated aqueous solution of sodium chloride, dried over magnesium sulfate and evaporated to give 2-t-butoxycarbonylmethoxyimino-2-(4-thiazolyl)acetic acid (syn isomer) (2.8 g), mp. 136°–139° C.

IR (Nujol): 1730 cm$^{-1}$

NMR (DMSO-d$_6$, δ): 1.46 (9H, s), 4.69 (2H, s), 8.08 (1H, d, J=2.0 Hz), 9.21 (1H, d, J=2.0 Hz)

Preparation 5

(1) To a solution of 2-t-butoxycarbonylmethoxyimino-2-(2-formamidothiazol-4-yl)acetic acid (syn isomer) (65.9 g) in ethyl acetate (300 ml) and tetrahydrofuran (200 ml) was dropwise added a solution of diphenyldiazomethane in ethyl acetate (1 m mol/ml, 200 ml) at ambient temperature and the mixture was stirred for an hour. The resultant mixture was washed with saturated aqueous solution of sodium bicarbonate and brine, and dried over magnesium sulfate. The solution was evaporated to give benzhydryl 2-t-butoxycarbonylmethoxyimino-2-(2-formamidothiazol-4-yl)acetate (syn isomer) (99.3 g). To the solution of benzhydryl 2-t-butoxycarbonylmethoxyimino-2-(2-formamidothiazol-4-yl)acetate (syn isomer) (99.0 g) in methanol (500 ml) was added conc. hydrochloric acid (41.6 g) at ambient temperature and the mixture was stirred at the same temperature for 1.5 hours. The reaction mixture was poured into a solution of sodium bicarbonate (33.6 g) in water (2.5 l) and extracted with ethyl acetate. The extracts were washed with brine and dried over magnesium sulfate. The solution was evaporated and the residue was pulverized with ether to give benzhydryl 2-t-butoxycarbonylmethoxyimino-2-(2-aminothiazol-4-yl)acetate (syn isomer) (72.3 g).

IR (Film): 1740, 1610 cm$^{-1}$

NMR (DMSO-d$_6$, δ): 1.43 (9H, s), 4.18 (2H, s), 6.73 (1H, s), 6.98 (1H, s), 7.07–7.60 (10H, m)

(2) A solution of t-butyl nitrite (1.7 g) in tetrahydrofuran (10 ml) was dropwise added to a solution of benzhydryl 2-t-butoxycarbonylmethoxyimino-2-(2-aminothiazol-4-yl)acetate (syn isomer) (5 g) in tetrahydrofuran (50 ml) at 50° to 53° C. under stirring and the mixture was stirred at the same temperature at 25 minutes. The reaction mixture was poured into a mixture of ethyl acetate and water and the organic layer was separated. The organic layer was washed with brine and dried over magnesium sulfate. The solution was evaporated and the residue was subjected to column chlomatography on silica gel. The elution was carried out with a mixture of benzene and ethyl acetate (19:1) and the eluates containing the object compound were evaporated to give benzhydryl 2-t-butoxycarbonylmethoxyimino-2-(4-thiazolyl)acetate (syn isomer) (2.2 g).

IR (Film): 1740, 1600 cm$^{-1}$

NMR (DMSO-d$_6$, δ): 1.43 (9H, s), 4.68 (2H, s), 7.08 (1H, s), 7.15–7.60 (10H, m), 8.03 (1H, d, J=2 Hz), 9.15 (1H, d, J=2 Hz)

(3) To a solution of benzhydryl 2-t-butoxycarbonylmethoxyimino-2-(4-thiazolyl)acetate (syn isomer) (2.2 g) and anisole (2.2 ml) in methylene chloride (22 ml) was added trifluoroacetic acid (4 ml) at ambient temperature and the mixture was stirred at the same temperature for 25 minutes. To the reaction mixture was added ethyl acetate and the solution was washed with water. To the separated organic layer was added water and the mixture was adjusted to pH 7.5 with 20% aqueous solution of sodium carbonate. The separated aqueous layer was acidified to pH 2.0 with 10% hydrochloric acid. The acidified solution was saturated with sodium chloride and extracted with ethyl acetate. The ethyl acetate layer was washed with brine, and dried over magnesium sulfate. The solution was evaporated and the residue was pulverized with diisopropyl ether and n-hexane to give 2-t-butoxycarbonylmethoxyimino-2-(4-thiazolyl)acetic acid (syn isomer) (1.07 g), mp. 136°–139° C.

IR (Nujol): 1730 cm$^{-1}$

EXAMPLE 1

Vilsmeier reagent was prepared from phosphorus oxychloride (0.76 g) and N,N-dimethylformamide (0.36 g) in ethyl acetate (1.44 ml) in a usual manner. 2-t-Butoxycarbonylmethoxyimino-2-(4-thiazolyl)acetic acid (syn isomer) (1.2 g) was added to the stirred suspension of Vilsmeier reagent in ethyl acetate (20 ml) under ice-cooling and the mixture was stirred for 20 minutes at the same temperature to prepare an activated acid solution. Trimethylsilylacetamide (3.5 g) was added to the stirred suspension of 7-amino-3-cephem-4-carboxylic acid (0.76 g) in tetrahydrofuran (15 ml) and the mixture was stirred for 20 minutes at 35° to 40° C. To the solution was added the above activated acid solution at −10° C. and the mixture was stirred for 30 minutes at the same temperature. Water was added to the reaction mixture and the separated organic layer was added to water and the mixture was adjusted to pH 7.5 with saturated aqueous solution of potassium carbonate. The separated aqueous layer was adjusted to pH 2.0 with 10% hydrochloric acid and extracted with ethyl acetate. The extracted layer was washed with saturated aqueous solution of sodium chloride, dried over magnesium sulfate and evaporated to give 7-[2-t-butoxycarbonylmethoxyimino-2-(4-thiazolyl)acetamido]-3-cephem-4-carboxylic acid (syn isomer) (1.4 g).

IR (Nujol): 3240, 1775, 1715, 1670, 1630 cm$^{-1}$

NMR (DMSO-d$_6$, δ): 1.44 (9H, s), 3.60 (2H, m), 4.61 (2H, s), 5.10 (1H, d, J=5.0 Hz), 5.86 (1H, dd, J=5.0 Hz, 8.0 Hz), 6.43 (1H, t, J=4.0 Hz), 7.88 (1H, d, J=2.0 Hz), 9.10 (1H, d, J=2.0 Hz), 9.49 (1H, d, J=8.0 Hz)

EXAMPLE 2

Vilsmeier reagent was prepared from phosphorus oxychloride (1.3 g) and N,N-dimethylformamide (0.6 g) in ethyl acetate (2.4 ml) in a usual manner. 2-t-Butoxycarbonylmethoxyimino-2-(4-thiazolyl)acetic acid (syn isomer) (2.0 g) was added to the stirred suspension of Vilsmeier reagent in ethyl acetate (20 ml) under ice-cooling and the mixture was stirred for 20 minutes at the same temperature to produce an activated acid solution.

Trimethylsilylacetamide (5.8 g) was added to the stirred suspension of 7-amino-3-methyl-3-cephem-4-carboxylic acid (1.4 g) in tetrahydrofuran (28 ml) and the mixture was stirred for 20 minutes at 38° to 42° C. To the solution was added the above activated acid solution at −10° C. and the mixture was stirred for 30 minutes at the same temperature. Water was added to the reaction mixture and the separated organic layer was added to water and the mixture was adjusted to pH 7.5 with a saturated aqueous solution of potassium carbonate. The separated aqueous layer was adjusted to pH 2.0 with 10% hydrochloric acid and extracted with ethyl acetate. The extract was washed with a saturated aqueous solution of sodium chloride, dried over magnesium sulfate and evaporated to give 7-[2-t-butoxycarbonylmethoxyimino-2-(4-thiazolyl)acetamido]-3-methyl-3-cephem-4-carboxylic acid (syn isomer) (2.25 g).

IR (Nujol): 1750 (broad), 1710, 1680 cm$^{-1}$

NMR (DMSO-$d_6$, $\delta$): 1.46 (9H, s), 2.02 (2H, s), 3.45 (2H, q, J=18.0 Hz), 4.61 (2H, s), 5.10 (1H, d, J=5.0 Hz), 5.73 (1H, dd, J=5.0 Hz, 8.0 Hz), 7.89 (1H, d, J=2.0 Hz), 9.10 (1H, d, J=2.0 Hz), 9.47 (1H, d, J=8.0 Hz)

EXAMPLE 3

Vilsmeier reagent was prepared from phosphorus oxychloride (2.2 g) and N,N-dimethylformamide (1.0 g) in ethyl acetate (4 ml) in a usual manner. 2-(Benzhydryloxycarbonylmethoxyimino)-2-(4-thiazolyl)acetic acid (syn isomer) (4.8 g) was added to the stirred suspension of Vilsmeier reagent in ethyl acetate (40 ml) under ice-cooling and the mixture was stirred for 30 minutes at the same temperature to prepare an activated acid solution. Trimethylsilylacetamide (10.1 g) was added to the stirred suspension of 7-amino-3-cephem-4-carboxylic acid (2.2 g) in tetrahydrofuran (30 ml) and the mixture was stirred for 30 minutes at 35° to 40° C. To the solution was added the above activated acid solution at −10° C. and the mixture was stirred at the same temperature for 30 minutes. Water was added to the reaction mixture and the separated organic layer was added to water and the mixture was adjusted to pH 7.5 with 20% aqueous solution of potassium carbonate. The separated aqueous layer was adjusted to pH 2.0 with 10% hydrochloric acid and extracted with ethyl acetate. The extract layer was washed with saturated aqueous solution of sodium chloride, dried over magnesium sulfate and evaporated to give 7-[2-benzhydryloxycarbonylmethoxyimino-2-(4-thiazolyl)acetamido]-3-cephem-4-carboxylic acid (syn isomer) (6.2 g).

IR (Nujol): 1775, 1720, 1675, 1630 cm$^{-1}$

NMR (DMSO-$d_6$, $\delta$): 3.56 (2H, m), 4.93 (2H, s), 5.13 (1H, d, J=5.0 Hz), 5.92 (1H, dd, J=5.0 Hz, 8.0 Hz), 6.48 (1H, m), 6.90 (1H, s), 7.11–7.65 (10H, s), 7.90 (1H, d, J=2.0 Hz), 9.16 (1H, d, J=2.0 Hz), 9.68 (1H, d, J=8 Hz)

EXAMPLE 4

The following compounds were obtained according to similar manners to those of Examples 1 to 3.

(1) 7-[2-Carboxymethoxyimino-2-(4-thiazolyl)acetamido]-3-methyl-3-cephem-4-carboxylic acid (syn isomer).

IR (Nujol): 1765, 1715, 1670 cm$^{-1}$ (2) 7-[2-t-Butoxycarbonylmethoxyimino-2-(4-thiazolyl)acetamido]-2-methyl-3-cephem-4-carboxylic acid (syn isomer).

IR (Nujol): 1780, 1720, 1670, 1630 cm$^{-1}$

NMR (DMSO-$d_6$, $\delta$): 1.28–1.67 (12H, m), 3.76 (1H, m), 4.62 (2H, s), 5.13 (1H, d, J=5.0 Hz), 5.92 (1H, dd, J=5.0 Hz), 8.0 Hz), 6.53 (1H, d, J=6.0 Hz), 7.90 (1H, d, J=2.0 Hz), 9.14 (1H, d, J=2.0 Hz), 9.53 (1H, d, J=8.0 Hz)

(3) 7-[2-Carboxymethoxyimino-2-(4-thiazolyl)acetamido]-2-methyl-3-cephem-4-carboxylic acid (syn isomer).

IR (Nujol): 1770, 1720, 1670, 1630 cm$^{-1}$ (4) 4-Nitrobenzyl 7-[2-t-butoxycarbonylmethoxyimino-2-(4-thiazolyl)acetamido]-3-methoxy-3-cephem-4-carboxylate (syn isomer).

IR (Nujol): 3230, 1770, 1710, 1675, 1600 cm$^{-1}$

NMR (DMSO-$d_6$, $\delta$): 1.43 (9H, s), 3.69 (2H, s), 3.80 (3H, s), 4.62 (2H, s), 5.19 (1H, d, J=4.0 Hz), 5.32 (2H, s), 5.65 (1H, dd, J=4.0 Hz, 8.0 Hz), 7.60 (2H, d, J=9.0 Hz), 7.94 (1H, d, J=2.0 Hz), 8.18 (2H, d, J=9.0 Hz), 9.11 (1H, d, J=2.0 Hz), 9.49 (1H, d, J=8.0 Hz)

(5) 7-[2-Carboxymethoxyimino-(4-thiazolyl)acetamido]-3-methoxy-3-cephem-4-carboxylic acid (syn isomer).

IR (Nujol): 3180, 1760, 1665 cm$^{-1}$ (6) 7-[2-t-Butoxycarbonylmethoxyimino-2-(4-thiazolyl)acetamido]-3-methoxy-3-cephem-4-carboxylic acid (syn isomer).

IR (Nujol): 1770, 1690 (broad) cm$^{-1}$ (7) 7-[2-t-Butoxycarbonylmethoxyimino-2-(4-thiazolyl)acetamido]cephalosporanic acid (syn isomer).

IR (Nujol): 3200, 1780, 1720, 1670 cm$^{-1}$

NMR (DMSO-$d_6$, $\delta$): 1.42 (9H, s), 2.01 (3H, s), 3.54 (2H, m), 4.62 (2H, s), 4.83 (2H, q, J=13.0 Hz), 5.16 (1H, d, J=5.0 Hz), 5.83 (1H, dd, J=5.0 Hz, 8.0 Hz), 7.89 (1H, d, J=2.0 Hz), 9.11 (1H, d, J=2.0 Hz), 9.53 (1H, d, J=8.0 Hz)

(8) 7-[2-Carboxymethoxyimino-2-(4-thiazolyl)acetamido]-cephalosporanic acid (syn isomer).

IR (Nujol): 3200, 1780, 1723, 1675 cm$^{-1}$ (9) Benzhydryl 7-[2-t-butoxycarbonylmethoxyimino-2-(4-thiazolyl)acetamido]-3-methylthiomethyl-3-cephem-4-carboxylate (syn isomer).

IR (Nujol): 3270, 1770, 1720, 1660 cm$^{-1}$

NMR (DMSO-$d_6$, $\delta$): 1.42 (9H, s), 1.78 (3H, s), 3.42–3.73 (4H, m), 4.61 (2H, s), 5.26 (1H, d, J=4.0 Hz), 5.87 (1H, dd, J=4.0 Hz, 8.0 Hz), 6.88 (1H, s), 7.13–7.60 (10H, m), 7.91 (1H, d, J=2.0 Hz), 9.11 (1H, d, J=2.0 Hz), 9.56 (1H, d, J=8.0 Hz)

(10) 7-[2-Carboxymethoxyimino-2-(4-thiazolyl)acetamido]-3-methylthiomethyl-3-cephem-4-carboxylic acid (syn isomer)

IR (Nujol): 3180, 1775, 1720, 1675 cm$^{-1}$

(11) Benzhydryl 7-[2-t-butoxycarbonylmethoxyimino-2-(4-thiazolyl)acetamido]-3-methoxymethyl-3-cephem-4-carboxylate (syn isomer).

IR (Nujol): 3250, 1780, 1720, 1655 cm$^{-1}$

NMR (DMSO-$d_6$, $\delta$): 1.43 (9H, s), 3.06 (3H, s), 3.56 (2H, m), 4.08 (2H, s), 4.63 (2H, s), 5.23 (1H, d, J=5.0 Hz), 5.91 (1H, dd, J=5.0 Hz, 8.0 Hz), 6.92 (1H, s), 7.17–7.62 (10H, m), 7.91 (1H, d, J=2.0 Hz), 9.12 (1H, d, J=2.0 Hz), 9.58 (1H, d, J=8.0 Hz)

(12) 7-[2-Carboxymethoxyimino-2-(4-thiazolyl)acetamido]-3-methoxymethyl-3-cephem-4-carboxylic acid (syn isomer).

IR (Nujol): 3200, 1775, 1720, 1675 cm$^{-1}$

(13) 7-[2-t-Butoxycarbonylmethoxyimino-2-(4-thiazolyl)acetamido]-3-chloro-3-cephem-4-carboxylic acid (syn isomer).

IR (Nujol): 1780, 1720, 1680 cm$^{-1}$

(14) 4-Nitrobenzyl 7-[2-t-butoxycarbonylmethoxyimino-2-(4-thiazolyl)acetamido]-3-chloro-3-cephem-4-carboxylate (syn isomer).

IR (Nujol): 1780, 1720, 1670, 1600 cm$^{-1}$

NMR (DMSO-d$_6$, δ): 1.43 (9H, s), 3.88 (2H, q, J=18.0 Hz), 4.63 (2H, s), 5.33 (1H, d, J=5.0 Hz), 5.45 (2H, s), 5.94 (1H, dd, J=5.0 Hz, 8.0 Hz), 7.67 (2H, d, J=8.0 Hz), 7.91 (1H, d, J=2.0 Hz), 8.23 (2H, d, J=8.0 Hz), 9.14 (1H, d, J=2.0 Hz), 9.67 (1H, d, J=8.0 Hz)

(15) 7-[2-Carboxymethoxyimino-2-(4-thiazolyl)acetamido]-3-chloro-3-cephem-4-carboxylic acid (syn isomer).

IR (Nujol): 3200, 1775, 1720, 1670 cm$^{-1}$

(16) Benzhydryl 7-[2-t-butoxycarbonylmethoxyimino-2-(4-thiazolyl)acetamido]-3-vinyl-3-cephem-4-carboxylate (syn isomer).

IR (Nujol): 3250, 1770, 1720, 1710, 1655 cm$^{-1}$

NMR (DMSO-d$_6$, δ): 1.44 (9H, s), 3.75 (2H, m), 4.64 (2H, s), 5.28 (1H, d, J=11.0 Hz), 5.29 (1H, d, J=5.0 Hz), 5.62 (1H, d, J=17.0 Hz), 5.93 (1H, dd, J=5.0 Hz, 8.0 Hz), 6.77 (1H, dd, J=11.0 Hz, 17.0 Hz), 6.93 (1H, s), 7.35 (10H, s), 7.93 (1H, d, J=2.0 Hz), 9.14 (1H, d, J=2.0 Hz), 9.62 (1H, d, J=8.0 Hz)

(17) 7-[2-Carboxymethoxyimino-2-(4-thiazolyl)acetamido]-3-vinyl-3-cephem-4-carboxylic acid (syn isomer).

IR (Nujol): 1765, 1710, 1665 cm$^{-1}$

(18) 7-[2-Carboxymethoxyimino-2-(4-thiazolyl)acetamido]-3-cephem-4-carboxylic acid (syn isomer).

IR (Nujol): 3280, 1750, 1725, 1655 cm$^{-1}$

(19) 1-Propionyloxyethyl 7-[2-benzhydryloxycarbonylmethoxyimino-2-(4-thiazolyl)acetamido]-3-cephem-4-carboxylate (syn isomer).

IR (Nujol): 1775, 1735, 1680 cm$^{-1}$

(20) 1-Ethoxycarbonyloxyethyl 7-[2-benzhydryloxycarbonylmethoxyimino-2-(4-thiazolyl)acetamido]-3-cephem-4-carboxylate (syn isomer).

IR (Nujol): 1780, 1750, 1680 cm$^{-1}$

(21) Pivaloyloxymethyl 7-[2-benzhydryloxycarbonylmethoxyimino-2-(4-thiazolyl)acetamido]-3-cephem-4-carboxylate (syn isomer).

IR (Nujol): 1780, 1740, 1680 cm$^{-1}$

(22) (5-Methyl-2-oxo-1,3-dioxol-4-yl)methyl 7-[2-benzhydryloxycarbonylmethoxyimino-2-(4-thiazolyl)acetamido]-3-cephem-4-carboxylate (syn isomer).

IR (Nujol): 1810, 1770, 1730, 1670 cm$^{-1}$

(23) 1-Propionyloxyethyl 7-[2-carboxymethoxyimino-2-(4-thiazolyl)acetamido]-3-cephem-4-carboxylate (syn isomer).

IR (Nujol): 3250, 1780, 1750, 1680 cm$^{-1}$

(24) 1-Ethoxycarbonyloxyethyl 7-[2-carboxymethoxyimino-2-(4-thiazolyl)acetamido]-3-cephem-4-carboxylate (syn isomer).

IR (Nujol): 1750 (broad), 1770 cm$^{-1}$

(25) Pivaloyloxymethyl 7-[2-carboxymethoxyimino-2-(4-thiazolyl)acetamido]-3-cephem-4-carboxylate (syn isomer).

IR (Nujol): 1740 (broad), 1680 cm$^{-1}$

(26) (5-Methyl-2-oxo-1,3-dioxol-4-yl)methyl 7-[2-carboxymethoxyimino-2-(4-thiazolyl)acetamido]-3-cephem-4-carboxylate (syn isomer).

IR (Nujol): 1810, 1770, 1730, 1670 cm$^{-1}$

EXAMPLE 5

Trifluoroacetic acid (5.2 ml) was added to a suspension of 7-[2-t-butoxycarbonylmethoxyimino-2-(4-thiazolyl)acetamido]-3-cephem-4-carboxylic acid (syn isomer) (1.3 g) in methylene chloride (2 ml) and anisole (1.3 ml) at ambient temperature and the mixture was stirred for 1.5 hours at the same temperature. To the resulting solution was added diisopropyl ether (40 ml) and n-hexane (30 ml) under stirring. The precipitates were collected by filtration, washed with solution of diisopropyl ether and n-hexane (1:1). The precipitates were added to a mixture of ethyl acetate and water and the mixture was adjusted to pH 7.5 with saturated aqueous solution of potassium carbonate. The separated aqueous layer was adjusted to pH 4.0 with 10% hydrochloric acid and the solution was washed with ethyl acetate. The resulting solution was adjusted to pH 1.8 with 10% hydrochloric acid under ice-cooling. The precipitates were collected by filtration, washed with cold water and dried over phosphorus pentoxide in vacuo to give 7-[2-carboxymethoxyimino-2-(4-thiazolyl)acetamido]-3-cephem-4-carboxylic acid (syn isomer) (1.0 g).

IR (Nujol): 3280, 1750, 1725, 1655, 1620 cm$^{-1}$

NMR (DMSO-d$_6$, δ): 3.58 (2H, m), 4.67 (2H, s), 5.12 (1H, d, J=4.0 Hz), 5.88 (1H, d, J=4.0 Hz, 8.0 Hz), 6.45 (1H, m), 7.93 (1H, d, J=2.0 Hz), 9.02 (1H, d, J=2.0 Hz), 9.52 (1H, d, J=8.0 Hz)

EXAMPLE 6

Trifluoroacetic aid (8.4 ml) was added to a suspension of 7-[2-t-butoxycarbonylmethoxyimino-2-(4-thiazolyl)acetamido]-3-methyl-3-cephem-4-carboxylic acid (syn isomer) (2.1 g) in methylene chloride (4.2 ml) and anisole (2.1 ml) at ambient temperature and the mixture was stirred for 1.5 hours at the same temperature. To the resultant solution was added diisopropyl ether (50 ml) and n-hexane (30 ml) and the mixture was stirred. The precipitates were collected by filtration, washed with a solution of diisopropyl ether and n-hexane (1:1). The precipitates were added to a mixture of ethyl acetate and water, and the mixture was adjusted to pH 7.0 with saturated aqueous solution of potassium carbonate. The separated aqueous layer was adjusted to pH 4 with 10% hydrochloric acid and the solution was washed with ethyl acetate. The aqueous layer was adjusted to pH 1.8 with 10% hydrochloric acid and saturated with sodium chloride. The acidic solution was extracted with ethyl acetate and tetrahydrofuran (1:1). The extract was washed with saturated aqueous solution of sodium chloride, dried over magnesium sulfate and evaporated to give 7-[2-carboxymethoxyimino-2-(4-thiazolyl)acetamido]-3-methyl-3-cephem-4-carboxylic acid (syn isomer) (1.0 g).

IR (Nujol): 1765, 1715, 1670 cm$^{-1}$

NMR (DMSO-d$_6$, δ): 2.03 (3H, s), 3.47 (2H, m), 4.67 (2H, s), 5.13 (1H, d, J=5.0 Hz), 5.78 (1H, dd, J=5.0 Hz, 8.0 Hz), 7.96 (1H, d, J=2.0 Hz), 9.15 (1H, d, J=2.0 Hz), 9.52 (1H, d, J=8.0 Hz)

EXAMPLE 7

Trifluoroacetic acid (1.4 ml) was added to a suspension of 1-propionyloxyethyl 7-[2-benzhydryloxycarbonylmethoxyimino-2-(4-thiazolyl)acetamido]-3-cephem-4-carboxylate (syn isomer) (1.2 g) in methylene chloride (10 ml) and anisole (0.8 ml) at ambient temperature and the mixture was stirred for 2 hours at the same temperature. To the resulting solution was added diisopropyl ether (50 ml) and the mixture was stirred. The precipitates were collected by filtration, washed with diisopropyl ether. The precipitates were added to a mixture of ethyl acetate and water, and the mixture was adjusted to pH 7.5 with 20% aqueous solution of potassium carbonate. The separated aqueous layer was adjusted to pH 2.0 with 10% hydrochloric acid and extracted with ethyl acetate. The extract layer was washed with saturated aqueous solution of sodium chloride, dried over magnesium sulfate and evaporated. The residue was washed with diisopropyl ether and filtered to give 1-propionyloxyethyl 7-[2-carboxymethoxyimino-2-(4-thiazolyl)acetamido]-3-cephem-4-carboxylate (syn isomer) (0.47 g).

IR (Nujol): 3250, 1780, 1750, 1680 cm$^{-1}$

NMR (DMSO-d$_6$, δ): 1.05 (3H, t, J=7.0 Hz), 1.49 (3H, d, J=5.0 Hz), 2.36 (2H, q, J=7.0 Hz), 3.63 (2H, m), 4.66 (2H, s), 5.16 (1H, d, J=4.0 Hz), 5.93 (1H, dd, J=4.0 Hz, 8.0 Hz), 6.59 (1H, t, J=4.0 Hz), 6.89 (1H, q, J=5.0 Hz), 7.93 (1H, d, J=2.0 Hz), 9.13 (1H, d, J=2.0 Hz), 9.54 (1H, d, J=8.0 Hz)

EXAMPLE 8

Trifluoroacetic acid (11.2 ml) was added to a stirred suspension of benzhydryl 7-[2-t-butoxycarbonylmethoxyimino-2-(4-thiazolyl)acetamido]-3-vinyl-3-cephem-4-carboxylate (syn isomer) (2.8 g) in methylene chloride (5.6 ml) and anisole (2.8 ml) at ambient temperature and the mixture was stirred for 1.5 hours at the same temperature. To the resultant solution was added diisopropyl ether (40 ml) and n-hexane (30 ml) and the mixture was stirred. The precipitates were collected by filtration, washed with a solution of diisopropyl ether and n-hexane (1:1). The precipitates were added to a mixture of ethyl acetate and water and the mixture was adjusted to pH 7.0 with a saturated aqueous solution of potassium carbonate. The separated aqueous layer was adjusted to pH 4.0 with 10% hydrochloric acid and the solution was washed with ethyl acetate. The aqueous layer was adjusted to pH 1.8 with 10% hydrochloric acid and saturated with sodium chloride. The acidic solution was extracted with ethyl acetate and tetrahydrofuran (1:1). The extract was washed with a saturated aqueous solution of sodium chloride, dried over magnesium sulfate and evaporated to give 7-[2-carboxymethoxyimino-2-(4-thiazolyl)acetamido]-3-vinyl-3-cephem-4-carboxylic acid (syn isomer) (1.22 g).

IR (Nujol): 1765, 1710, 1665 cm$^{-1}$

NMR (DMSO-d$_6$, δ): 3.71 (2H, m), 4.72 (2H, s), 5.26 (1H, d, J=5.0 Hz), 5.37 (1H, d, J=11.0 Hz), 5.61 (1H, d, J=17.0 Hz), 5.91 (1H, dd, J=5.0 Hz, 8.0 Hz), 6.98 (1H, dd, J=11.0 Hz, 17.0 Hz), 8.02 (1H, d, J=2.0 Hz), 9.21 (1H, d, J=2.0 Hz), 9.64 (1H, d, J=8.0 Hz)

Further disodium 7-[2-carboxylatomethoxyimino-2-(4-thiazolyl)acetamido]-3-vinyl-3-cephem-4-carboxylate (syn isomer) was obtained by reacting 7-[2-carboxymethoxyimino-2-(4-thiazolyl)acetamido]-3-vinyl-3-cephem-4-carboxylic acid (syn isomer) with sodium bicarbonate in a usual manner.

EXAMPLE 9

The following compounds were obtained according to similar manners to those of Examples 5 to 8.

(1) 7-[2-Carboxymethoxyimino-2-(4-thiazolyl)acetamido]-2-methyl-3-cephem-4-carboxylic acid (syn isomer).

IR (Nujol): 1770, 1720, 1670, 1630 cm$^{-1}$

NMR (DMSO-d$_6$, δ): 1.43 (3H, d, J=7.0 Hz), 3.72 (1H, m), 4.67 (2H, s), 5.13 (1H, d, J=4.0 Hz), 5.93 (1H, dd, J=4.0 Hz, 8.0 Hz), 6.55 (1H, d, J=6.0 Hz), 7.92 (1H, d, J=2.0 Hz), 9.12 (1H, d, J=2.0 Hz), 9.53 (1H, d, J=8.0 Hz)

(2) 7-[2-Carboxymethoxyimino-2-(4-thiazolyl)acetamido]-3-methoxy-3-cephem-4-carboxylic acid (syn isomer).

IR (Nujol): 3180, 1760, 1665 cm$^{-1}$

NMR (DMSO-d$_6$, δ): 3.60 (2H, broad s), 3.75 (3H, s), 4.68 (2H, s), 5.18 (1H, d, J=5.0 Hz), 5.62 (1H, dd, J=5.0 Hz, 8.0 Hz), 8.02 (1H, d, J=2.0 Hz), 9.15 (1H, d, J=2.0 Hz), 9.52 (1H, d, J=8.0 Hz)

(3) 7-[2-Carboxymethoxyimino-2-(4-thiazolyl)acetamido]-cephalosporanic acid (syn isomer).

IR (Nujol): 3200, 1780, 1723, 1675 cm$^{-1}$

NMR (DMSO-d$_6$, δ): 2.01 (3H, s), 3.56 (2H, m), 4.67 (2H, s), 4.83 (2H, q, J=14.0 Hz), 5.17 (1H, d, J=4.0 Hz), 5.85 (1H, dd, J=4.0 Hz, 8.0 Hz), 7.92 (1H, d, J=2.0 Hz), 9.12 (1H, d, J=2.0 Hz), 9.54 (1H, d, J=8.0 Hz)

(4) 7-[2-Carboxymethoxyimino-2-(4-thiazolyl)acetamido]-3-methylthiomethyl-3-cephem-4-carboxylic acid. (syn isomer).

IR (Nujol): 3180, 1775, 1720, 1675 cm$^{-1}$

NMR (DMSO-d$_6$, δ): 1.96 (3H, s), 3.47–3.76 (4H, m), 4.67 (2H, s), 5.20 (1H, d, J=4.0 Hz), 5.79 (1H, dd, J=4.0 Hz, 8.0 Hz), 7.93 (1H, d, J=2.0 Hz), 9.12 (1H, d, J=2.0 Hz), 9.54 (1H, d, J=8.0 Hz)

(5) 7-[2-Carboxymethoxyimino-2-(4-thiazolyl)acetamido]-3-methoxymethyl-3-cephem-4-carboxylic acid (syn isomer).

IR (Nujol): 3200, 1775, 1720, 1675 cm$^{-1}$

NMR (DMSO-d$_6$, δ): 3.27 (3H, s), 3.52 (2H, m), 4.16 (2H, s), 4.66 (2H, s), 5.16 (1H, d, J=4.0 Hz), 5.81 (1H, dd, J=4.0 Hz, 8.0 Hz), 7.91 (1H, d, J=2.0 Hz), 9.11 (1H, d, J=2.0 Hz), 9.52 (1H, d, J=8.0 Hz)

(6) 7-[2-Carboxymethoxyimino-2-(4-thiazolyl)acetamido]-3-chloro-3-cephem-4-carboxylic acid (syn isomer).

IR (Nujol): 3200, 1775, 1720, 1670 cm$^{-1}$

NMR (DMSO-d$_6$, δ): 3.81 (2H, q, J=18.0 Hz), 4.66 (2H, s), 5.25 (1H, d, J=5.0 Hz), 5.87 (1H, dd, J=5.0 Hz, 8.0 Hz), 7.72 (1H, d, J=2.0 Hz), 9.10 (1H, d, J=2.0 Hz), 9.63 (1H, d, J=8.0 Hz)

(7) 1-Ethoxycarbonyloxyethyl 7-[2-carboxymethoxyimino-2-(4-thiazolyl)acetamido]-3-cephem-4-carboxylate (syn isomer).

IR (Nujol): 1750 (broad), 1770 cm$^{-1}$

NMR (DMSO-d$_6$, δ) 1.09 and 1.22 (Total 3H, each t, J=7.0 Hz), 1.50 (3H, d, J=5.0 Hz), 3.63 (2H, m), 4.16 (2H, q, J=7.0 Hz), 4.66 (2H, s), 5.16 (1H, d, J=4.0 Hz), 5.93 (1H, m), 6.62 (1H, t, J=4.0 Hz), 6.77 (1H, q, J=5.0 Hz), 7.94 (1H, d, J=2.0 Hz), 9.14 (1H, d, J=2.0 Hz), 9.56 (1H, d, J=8.0 Hz)

(8) Pivaloyloxymethyl 7-[2-carboxymethoxyimino-2-(4-thiazolyl)acetamido]-3-cephem-4-carboxylate (syn isomer).

IR (Nujol): 1740 (broad), 1680 cm$^{-1}$

NMR (DMSO-d$_6$, δ): 1.14 (9H, s), 3.60 (2H, q, J=18.0 Hz), 4.63 (2H, s), 5.13 (1H, d, J=4.0 Hz), 5.62-6.03 (3H, m), 6.55 (1H, t, J=4.0 Hz), 7.87 (1H, d, J=2.0 Hz), 9.06 (1H, d, J=2.0 Hz), 9.48 (1H, d, J=8.0 Hz)

(9) (5-Methyl-2-oxo-1,3-dioxol-4-yl)methyl 7-[2-carboxymethoxyimino-2-(4-thiazolyl)acetamido]-3-cephem-4-carboxylate (syn isomer).

IR (Nujol): 1810, 1770, 1730, 1670 cm$^{-1}$

NMR (DMSO-d$_6$, δ): 2.18 (3H, s), 3.62 (2H, m), 4.67 (2H, s), 5.15 (2H, s), 5.16 (1H, d, J=5.0 Hz), 5.93 (1H, dd, J=5.0 Hz, 8.0 Hz), 6.60 (1H, t, J=4.0 Hz), 7.95 (1H, d, J=2.0 Hz), 9.15 (1H, d, J=2.0 Hz), 9.56 (1H, d, J=8.0 Hz)

EXAMPLE 10

4-Nitrobenzyl 7-[2-t-butoxycarbonylmethoxyimino-2-(4-thiazolyl)acetamido]-3-methoxy-3-cephem-4-carboxylate (syn isomer) (2.9 g) was dissolved in a mixed solution of methanol (50 ml), tetrahydrofuran (30 ml) and glacial acetic acid (0.5 ml). After adding 10% palladium on carbon (1.5 g) to the solution, the mixture was subjected to catalytic reduction at ambient temperature under atmospheric pressure. The catalyst was filtered off and the filtrate was concentrated under reduced pressure. Water and ethyl acetate were added to the residue and the mixture was adjusted to pH 7.5 with a saturated aqueous solution of potassium carbonate. The separated aqueous layer was adjusted to pH 2.0 with 10% hydrochloric acid and extracted with ethyl acetate. The extract was washed with a saturated aqueous solution of sodium chloride, dried over magnesium sulfate and evaporated to give 7-[2-t-butoxycarbonylmethoxyimino-2-(4-thiazolyl)acetamido]-3-methoxy-3-cephem-4-carboxylic acid (syn isomer) (1.71 g).

IR (Nujol): 1770, 1690 (broad) cm$^{-1}$

NMR (DMSO-d$_6$, δ): 1.44 (9H, s), 3.60 (2H, s), 3.75 (3H, s), 4.63 (2H, s), 5.16 (1H, d, J=4.0 Hz), 5.61 (1H, dd, J=4.0 Hz, 8.0 Hz), 7.96 (1H, d, J=2.0 Hz), 9.13 (1H, d, J=2.0 Hz), 9.50 (1H, d, J=8.0 Hz)

EXAMPLE 11

The following compounds were obtained according to a similar manner to that of Example 10.

(1) 7-[2-t-Butoxycarbonylmethoxyimino-2-(4-thiazolyl)-acetamido]-3-methyl-3-cephem-4-carboxylic acid (syn isomer).

IR (Nujol): 1750 (broad), 1710, 1680 cm$^{-1}$ (2) 7-[2-Carboxymethoxyimino-2-(4-thiazolyl)acetamido]-3-methyl-3-cephem-4-carboxylic acid (syn isomer).

IR (Nujol): 1765, 1715, 1670 cm$^{-1}$ (3) 7-[2-t-Butoxycarbonylmethoxyimino-2-(4-thiazolyl)acetamido]-2-methyl-3-cephem-4-carboxylic acid (syn isomer).

IR (Nujol): 1780, 1720, 1670, 1630 cm$^{-1}$ (4) 7-[2-Carboxymethoxyimino-2-(4-thiazolyl)acetamido]-2-methyl-3-cephem-4-carboxylic acid (syn isomer).

IR (Nujol): 1770, 1720, 1670, 1630 cm$^{-1}$ (5) 7-[2-Carboxymethoxyimino-2-(4-thiazolyl)acetamido]-3-methoxy-3-cephem-4-carboxylic acid (syn isomer).

IR (Nujol): 3180, 1760, 1665 cm$^{-1}$ (6) 7-[2-t-Butoxycarbonylmethoxyimino-2-(4-thiazolyl)-acetamido]cephalosporanic acid (syn isomer).

IR (Nujol): 3200, 1780, 1720, 1670 cm$^{-1}$ (7) 7-[2-Carboxymethoxyimino-2-(4-thiazolyl)acetamido]-cephalosporanic acid (syn isomer).

IR (Nujol): 3200, 1780, 1723, 1675 cm$^{-1}$ (8) 7-[2-Carboxymethoxyimino-2-(4-thiazolyl)acetamido]-3-methylthiomethyl-3-cephem-4-carboxylic acid (syn isomer).

IR (Nujol): 3180, 1775, 1720, 1675 cm$^{-1}$ (9) 7-[2-Carboxymethoxyimino-2-(4-thiazolyl)acetamido]-3-methoxymethyl-3-cephem-4-carboxylic acid (syn isomer).

IR (Nujol): 3200, 1775, 1720, 1675 cm$^{-1}$

(10) 7-[2-t-Butoxycarbonylmethoxyimino-2-(4-thiazolyl)-acetamido]-3-chloro-3-cephem-4-carboxylic acid (syn isomer).

IR (Nujol): 1780, 1720, 1680 cm$^{-1}$

NMR (DMSO-d$_6$, δ): 1.43 (9H, s), 3.81 (2H, q, J=18.0 Hz), 4.61 (2H, s), 5.26 (1H, d, J=5.0 Hz), 5.86 (1H, dd, J=5.0 Hz, 8.0 Hz), 7.99 (1H, d, J=2.0 Hz), 9.12 (1H, d, J=2.0 Hz), 9.64 (1H, d, J=8 Hz)

(11) 7-[2-Carboxymethoxyimino-2-(4-thiazolyl)acetamido]-3-chloro-3-cephem-4-carboxylic acid (syn isomer).

IR (Nujol): 3200, 1775, 1720, 1670 cm$^{-1}$

(12) 7-[2-Carboxymethoxyimino-2-(4-thiazolyl)acetamido]-3-vinyl-3-cephem-4-carboxylic acid (syn isomer).

IR (Nujol): 1765, 1710, 1665 cm$^{-1}$

(13) 7-[2-t-Butoxycarbonylmethoxyimino-2-(4-thiazolyl)-acetamido]-3-cephem-4-carboxylic acid (syn isomer).

IR (Nujol): 3240, 1775, 1715, 1670, 1630 cm$^{-1}$

(14) 7-[2-Carboxymethoxyimino-2-(4-thiazolyl)acetamido]-3-cephem-4-carboxylic acid (syn isomer).

IR (Nujol): 3280, 1750, 1725, 1655, 1620 cm$^{-1}$

(15) 7-[2-Benzhydryloxycarbonylmethoxyimino-2-(4-thiazolyl)acetamido]-3-cephem-4-carboxylic acid (syn isomer).

IR (Nujol): 1775, 1720, 1675, 1630 cm$^{-1}$

EXAMPLE 12

1-Chloroethyl propionate (0.6 g) was added to the mixture of 7-[2-benzhydryloxycarbonylmethoxyimino-2-(4-thiazolyl)acetamido]-3-cephem-4-carboxylic acid (syn isomer) (2.0 g) in dimethyl sulfoxide (13 ml) and potassium carbonate (0.3 g) and the mixture was stirred for 2 hours at 40° C. The reaction mixture was added to the mixture of ice-water and ethyl acetate and the mixture was adjusted to pH 7.5 with 20% aqueous solution of potassium carbonate. The separated organic layer was washed with water, dried over magnesium sulfate and evaporated to give 1-propionyloxyethyl 7-[2-benzhydryloxycarbonylmethoxyimino-2-(4-thiazolyl)acetamido]-3-cephem-4-carboxylate (syn isomer) (1.3 g).

IR (Nujol): 1775, 1735, 1680 cm$^{-1}$

NMR (DMSO-d$_6$, δ): 1.04 (3H, t, J=7.0 Hz), 1.51 (3H, d, J=5.0 Hz), 2.38 (2H, q, J=7.0 Hz), 3.60 (2H, m), 4.94 (2H, s), 5.18 (1H, d, J=4.0 Hz), 5.96 (1H, dd, J=4.0 Hz, 8.0 Hz), 6.63 (1H, t, J=4.0 Hz), 6.91 (1H, s), 6.93 (1H, q, J=5.0 Hz), 7.20–7.59 (10H, m), 7.92 (1H, d, J=2.0 Hz), 9.18 (1H, d, J=2.0 Hz), 9.68 (1H, d, J=8.0 Hz)

EXAMPLE 13

4-Bromomethyl-5-methyl-1,3-dioxol-2-one (0.5 g) was added to the mixture of 7-[2-benzhydryloxycarbonylmethoxyimino-2-(4-thiazolyl)acetamido]-3-cephem-4-carboxylic acid (syn isomer) (1.0 g) in dimethylsulfoxide (7 ml) and potassium carbonate (0.17 g) and the mixture was stirred for 2 hours at ambient temperature. The reaction mixture was added to the mixture of ice-water and ethyl acetate and the mixture was adjusted to pH 7.5 with 20% aqueous solution of potassium carbonate. The separated organic layer was washed with water and dried over magnesium sulfate. The crude product obtained by concentration was purified by silica gel column chromatography using ethyl acetate and n-hexane (rate=3:2) as eluates.

The eluted fractions were evaporated to give (5-methyl-2-oxo-1,3-dioxol-4-yl)methyl 7-[2-benzhydryloxycarbonylmethoxyimino-2-(4-thiazolyl)acetamido]-3-cephem-4-carboxylate (syn isomer) (0.37 g).

IR (Nujol): 1810, 1770, 1730, 1670 cm$^{-1}$

NMR (DMSO-d$_6$, δ): 2.14 (3H, s), 3.53 (2H, m), 4.86 (2H, s), 5.09 (2H, s), 5.10 (1H, d, J=5.0 Hz), 5.88 (1H, dd, J=5.0 Hz, 8.0 Hz), 6.51 (1H, t, J=4.0 Hz), 6.81 (1H, s), 7.09–7.50 (10H, s), 7.80 (1H, d, J=2.0 Hz), 9.06 (1H, d, J=2.0 Hz), 9.57 (1H, d, J=8.0 Hz)

EXAMPLE 14

The following compounds were obtained according to similar manners to those of Examples 12 and 13.

(1) 4-Nitrobenzyl 7-[2-t-butoxycarbonylmethoxyimino-2-(4-thiazolyl)acetamido]-3-methoxy-3-cephem-4-carboxylate (syn isomer).

IR (Nujol): 3230, 1770, 1710, 1675, 1600 cm$^{-1}$ (2) Benzhydryl 7-[2-t-butoxycarbonylmethoxyimino-2-(4-thiazolyl)acetamido]-3-methylthiomethyl-3-cephem-4-carboxylate (syn isomer).

IR (Nujol): 3270, 1770, 1720, 1660 cm$^{-1}$ (3) Benzhydryl 7-[2-t-butoxycarbonylmethoxyimino-2-(4-thiazolyl)acetamido]-3-methoxymethyl-3-cephem-4-carboxylate (syn isomer).

IR (Nujol): 3250, 1780, 1720, 1655 cm$^{-1}$ (4) 4-Nitrobenzyl 7-[2-t-butoxycarbonylmethoxyimino-2-(4-thiazolyl)acetamido]-3-chloro-3-cephem-4-carboxylate (syn isomer).

IR (Nujol): 1780, 1720, 1670, 1600 cm$^{-1}$ (5) Benzhydryl 7-[2-t-butoxycarbonylmethoxyimino-2-(4-thiazolyl)acetamido]-3-vinyl-3-cephem-4-carboxylate (syn isomer).

IR (Nujol): 3250, 1770, 1720, 1710, 1655 cm$^{-1}$ (6) 1-Ethoxycarbonyloxyethyl 7-[2-benzhydryloxycarbonylmethoxyimino-2-(4-thiazolyl)acetamido]-3-cephem-4-carboxylate (syn isomer).

IR (Nujol): 1780, 1750, 1680 cm$^{-1}$

NMR (DMSO-d$_6$, δ): 1.09 (3H, t, J=7.0 Hz), 1.52 (3H, d, J=5.0 Hz), 3.63 (2H, m), 4.17 (2H, q, J=7.0 Hz), 4.93 (2H, s), 5.17 (1H, d, J=5.0 Hz), 5.97 (1H, dd, J=5.0 Hz, 8.0 Hz), 6.65 (1H, t, J=4.0 Hz), 6.81 (1H, q, J=5.0 Hz), 6.92 (1H, s), 7.20–7.60 (10H, m), 7.92 (1H, d, J=2.0 Hz), 9.68 (1H, d, J=8.0 Hz), 9.19 (1H, d, J=2.0 Hz)

(7) Pivaloyloxymethyl 7-[2-benzhydryloxycarbonylmethoxyimino-2-(4-thiazolyl)acetamido]-3-cephem-4-carboxylate (syn isomer).

IR (Nujol): 1780, 1740, 1680 cm$^{-1}$

NMR (DMSO-d$_6$, δ): 1.16 (9H, s), 3.61 (2H, m), 4.91 (2H, s), 5.16 (1H, d, J=4.0 Hz), 5.69–6.04 (3H, m), 6.59 (1H, m), 6.89 (1H, s), 7.16–7.60 (10H, m), 7.89 (1H, d, J=2.0 Hz), 9.16 (1H, d, J=2.0 Hz), 9.68 (1H, d, J=7.0 Hz)

(8) 1-Propionyloxyethyl 7-[2-carboxymethoxyimino-2-(4-thiazolyl)acetamido]-3-cephem-4-carboxylate (syn isomer).

IR (Nujol): 3250, 1780, 1750, 1680 cm$^{-1}$ (9) 1-Ethoxycarbonyloxyethyl 7-[2-carboxymethoxyimino-2-(4-thiazolyl)acetamido]-3-cephem-4-carboxylate (syn isomer).

IR (Nujol): 1750 (broad), 1770 cm$^{-1}$

(10) Pivaloyloxymethyl 7-[2-carboxymethoxyimino-2-(4-thiazolyl)acetamido]-3-cephem-4-carboxylate (syn isomer).

IR (Nujol): 1740 (broad), 1680 cm$^{-1}$

(11) (5-Methyl-2-oxo-1,3-dioxol-4-yl)methyl 7-[2-carboxymethoxyimino-2-(4-thiazolyl)acetamido]-3-cephem-4-carboxylate (syn isomer).

IR (Nujol): 1810, 1770, 1730, 1670 cm$^{-1}$

What we claim is:

1. A compound of the formula:

wherein
R$^1$ carboxy(lower)alkyl or protected carboxy(lower)alkyl, and
R$^2$ is carboxy or protected carboxy, and pharmaceutically acceptable salts thereof.

2. A compound of claim 1, wherein
R$^1$ is carboxy(lower)alkyl or esterified carboxy(lower)alkyl, and
R$^2$ is carboxy or esterified carboxy.

3. Syn isomer of a compound of claim 2.

4. A compound of claim 3, wherein R$^1$ is carboxy(lower)alkyl or lower alkoxycarbonyl(lower)alkyl, and R$^2$ is carboxy.

5. A compound of claim 4, which is 7-[2-carboxymethoxyimino-2-(4-thiazolyl)acetamido]-3-cephem-4-carboxylic acid (syn isomer).

6. An antibacterial composition comprising an effective amount of a compound of claim 1 in association with a pharmaceutically acceptable substantially non-toxic carrier or excipient.

* * * * *